(12) United States Patent
Chuang et al.

(10) Patent No.: US 9,532,743 B2
(45) Date of Patent: Jan. 3, 2017

(54) APPARATUS FOR DETECTING TISSUE HARDNESS OF LIVING BODY

(71) Applicants: SOUTHERN TAIWAN UNIVERSITY OF SCIENCE AND TECHNOLOGY, Tainan (TW); KUANG TAI METAL INDUSTRIAL CO., LTD., Tainan (TW)

(72) Inventors: Cheng Hsin Chuang, Tainan (TW); Wen Chen Huang, Tainan (TW); Tsan Hsiu Li, Tainan (TW)

(73) Assignees: Southern Taiwan University of Science and Technology, Tainan (TW); Kuang Tai Metal Industrial Co., Ltd., Tainan (TW)

( * ) Notice: Subject to any disclaimer, the term of this patent is extended or adjusted under 35 U.S.C. 154(b) by 96 days.

(21) Appl. No.: 14/534,767

(22) Filed: Nov. 6, 2014

(65) Prior Publication Data
US 2016/0128622 A1    May 12, 2016

(51) Int. Cl.
*A61B 5/151* (2006.01)
*G01N 33/66* (2006.01)
*A61B 5/00* (2006.01)

(52) U.S. Cl.
CPC ............ *A61B 5/442* (2013.01); *A61B 5/0053* (2013.01)

(58) Field of Classification Search
CPC .............................. A61B 5/442; A61B 5/0053
See application file for complete search history.

(56) References Cited

U.S. PATENT DOCUMENTS

| | | | | |
|---|---|---|---|---|
| 5,820,602 A | * | 10/1998 | Kovelman | A61M 5/172 604/156 |
| 2013/0122466 A1 | * | 5/2013 | Connor | A61B 5/0053 433/215 |

* cited by examiner

*Primary Examiner* — Michael C Stout
*Assistant Examiner* — Nicholas E Kolderman
(74) *Attorney, Agent, or Firm* — Rosenberg, Klein & Lee

(57) ABSTRACT

An apparatus for detecting tissue hardness of a living body includes a housing, a cap, a bottom cover, a driving module, a buffering module, a spring pipeline, a push-rod and a detecting module, and the driving module includes a firing spring and a restoring spring, and the two springs have different rigidities so as to form a reciprocating structure of the firing mechanism. After the detecting module of a firing mechanism is triggered, the resilience of the restoring spring compresses the firing spring back to its firing length, so as to restore its position by a single driving point and allow users to complete the firing operation by one hand and simplify the operation of doctors to improve convenience and efficiency.

4 Claims, 11 Drawing Sheets

US 9,532,743 B2

APPARATUS FOR DETECTING TISSUE HARDNESS OF LIVING BODY

FIELD OF THE INVENTION

The present invention relates to a detecting apparatus, in particular to an apparatus applied in an endoscope accessory and having a detecting element for detecting and measuring tissue hardness in a living body.

BACKGROUND OF THE INVENTION

In general, tumors are found through touching or naked-eye observation, and the observation is usually assisted by instruments such as ultrasonic instruments or endoscopes. The endoscope primarily extends a soft tube with a camera and a light source device into a living body, and an external display device is provided for obtaining the information of the surfaces of organs and tissues in vivo. Further, a tissue section is sliced and collected in order to perform a pathological test. However, the endoscope just can provide the information of the surface of tissues only, but it is difficult to determine the existence of a tumor in subcutaneous tissues through the observation by the endoscope.

A change of tissue hardness is usually accompanied with a pathological change. For example, a subcutaneous tumor causes abnormal tissue hardness, and the test still requires ultrasonic endoscopes to obtain tumor information accurately. However, the ultrasonic endoscope is expensive and thus it is not popular among general medical institutions. Therefore, it is necessary to provide a simple and easy way of measuring the flexibility of tissues in a living body in order to examine whether there is a subcutaneous tumor and assist the diagnosis of diseases.

As disclosed in U.S. Pat. No. 8,328,730 entitled "Living body measurement apparatus", the living body measurement apparatus includes a contact section which includes a first contact surface contacting a living body and which applies pressure to the living body, an auxiliary section disposed on an external side of the contact section and including a second contact surface contacting the living body, and supporting the second contact surface, so that the second contact surface performs reciprocating movement between coplanar positions and drives the second contact surface to retract to the position of the first contact surface, and the first contact surface and the second contact surface are disposed on the same plane, and a first pressure sensor is installed for measuring pressure applied to both of the contact section and the auxiliary section. The measurement apparatus includes a support section for supporting the auxiliary section, a first elongated groove formed between the auxiliary section and the support section and extended in a reciprocating direction of the reciprocating movement of the second contact surface, a second elongated groove which is formed in the one of the auxiliary section and the support section and which extends in a direction perpendicular to the reciprocating direction, a protruding portion which is formed in the other of the auxiliary section and the support section and which is disposed at either one of the first elongated groove, so that the locking mechanism is configured to lock the auxiliary section in a state in which the second contact surface is disposed at the retracted position, such that the hardness of muscular tissues and the pain of a patient can be measured by a single instrument.

As disclosed in U.S. Pat. No. 4,159,640 entitled "Apparatus for measuring the consistency or hardness of a material", the apparatus includes a cylindrical housing enclosing a spring with the degree of pre-straining of which, in compression, is adjustable by means of screw, and the spring pushes a piston towards the material, and the end of the piston fixedly carries a feeler, and the displacement of the piston in the cylindrical housing is registered by means of a conventional type of displacement sensor which delivers a continuous voltage output proportional to the displacement of the feller from a reference position, and the housing includes stops for limiting the travel of the piston, thereby defining the aforementioned reference position. Therefore, this apparatus can be used for testing a material having variable pressures and measuring the hardness of elastic material (such as skin) accurately.

As disclosed in U.S. Pat. No. 5,766,137 entitled "Frequency deviation detecting circuit and measuring apparatus using the frequency deviation detecting circuit", the apparatus includes an oscillator for generating a mechanical oscillation, and a detecting element for detecting the oscillation information, and a feedback circuit for feeding back a feedback signal of the oscillator based on the oscillation information, and driving the oscillator into a first resonant state, and the oscillator has a central frequency of the first oscillator, a gain variation compensating circuit installed to the feedback circuit, and the central frequency of the gain is different from the frequency of the oscillator applicable for increasing the gain in response to a change of frequency. If the frequency changes, the oscillator shifts from the first resonant state to a second resonant state, and the oscillator has a second oscillation central frequency, and the apparatus detects the deviation between the central frequencies of the first and second oscillators, and this apparatus is applied to the apparatus for measuring hardness and detecting the hardness of biological tissue (such as skin or internal organ).

In addition, the inventor of the present invention also filed a sensor related patent as disclosed in U.S. patent application Ser. No. 13/116,092 entitled "Apparatus and method for identifying a tissue in a living body", and the apparatus comprises a sensing element for sensing tissue parameters, a manipulating device for manipulating the sensing element, and an analyzing element for analyzing the meaning of the parameters. The sensing element is placed near an object to be tested and forces are applied to both of the top and bottom ends of the sensing element, so that a contact force is produced between soft tissues and the sensing element to cause deformation, and the deformation is measured and its corresponsive voltage value is read, so that a ratio of voltage values or a reflected stress ratio may be used to estimate the tissue to be tested and the material property related to hardness.

However, the aforementioned patent primarily aims at the aspect of sensors, and the control of forces is essential to the sensors, so that the sensors still require an appropriate firing device for triggering the sensor and touching the object to be tested in order to obtain measured values and continue the measurement.

SUMMARY OF THE INVENTION

In view of the drawback of the conventional endoscope that can provide the information of the surfaces of organs and tissues only, and the drawbacks of the aforementioned patents that focus on the sensor only and seldom have any improvement to the sensor and the firing mechanism and affect major components for operating the sensor or even affect the measurement data and diagnosis results, it is a primary objective of the present invention to provide a firing mechanism that uses two springs of different rigidities to constitute a reciprocating structure of the firing mechanism, so that after the sensor of the firing mechanism is triggered, the position restoration can be achieved by a by a single driving point, and the operation can be completed by one hand to simplify the operation and improve the convenience and efficiency.

Another objective of the present invention is to reduce the noise generated from the vibration of the sensor by winding and fixing conductive wires of a detective module to a core wire, so as to obtain more accurate measurements and data.

To achieve the aforementioned objectives, the present invention provides an apparatus for detecting tissue hardness of a living body, the apparatus comprises a housing, a cap, a bottom cover, a driving module, a buffering module, a spring pipeline, a push-rod and a detecting module, wherein the housing is a hollow tube and the housing has an outer embedding wall formed around the periphery of the housing, an inner embedding wall formed inside the housing, and a fixed base formed in a tube body of the housing; the cap is embedded into the outer embedding wall of the housing and has an opening; the bottom cover is coupled to the housing, and having a pipeline formed therein, a connecting portion disposed on a side of the bottom cover, and a through hole formed at the connecting portion; and the driving module comprises: a pressing device which is in form of a hollow tube and has a triggering rod extended separately from both sides of the pressing device; a pull-rod installed in the hollow tube of the pressing device; a restoring spring, installed between the pressing device and the fixed base of the housing; a trigger, fixed to the pull-rod, and having an elastic brace formed separately on both sides of the trigger, such that the elastic brace supports and abuts the inner embedding wall of the housing; and a firing spring, installed between the fixed base of the housing and the trigger; and the buffering module comprises: a seat body, disposed at an end of the housing, and having a penetrating hole; and a buffer spring, sheathed on the seat body; and the spring pipeline, being installed in the pipeline of the bottom cover, and the push-rod passing into the spring pipeline and having a front end fixed to the trigger, and a detecting module, combined with an end of the push-rod , and including: a front carrier, having a perforation and a plurality of holes; a spring duct, having a core wire fixed therein; a rear carrier, having a plurality of holes, and a conductive silver paste filled into the holes; a sensor, combined with the rear carrier; a plurality of conductive wires, wound around the core wire, such that after an end of the conductive wire passes through the hole of the rear carrier, the end of the conductive wire is coupled to the sensor, and after the other end of the conductive wire passes through the hole of the front carrier, said other end is passed out of the perforation and connected to a back-end system for reading a signal; and a waterproof layer, coated around the periphery of the rear carrier and the spring duct.

By pressing down the pressing device, the pressing device compresses the restoring spring, while driving the triggering rod of the pressing device to inwardly push the elastic brace of the trigger and allow the trigger and the pull-rod to fall, so as to release the compressed state of the firing spring. While the trigger is falling, the push-rod is linked and pushed out, so that a detecting module combined with an end of the push-rod to push the sensor touches a tissue to be tested. When the trigger falls to the seat body, a buffer spring of the seat body provides a buffer to the downward pulling force. Till the detecting module detects a signal and transmits the signal to a back-end system, the pressing device may be released, so that the restoring spring is released from the compressed state to push the pressing device back to its original position, and the pull-rod pulls back the trigger, so that the elastic brace of the trigger abuts the inner embedding wall of the housing to set the firing spring to the compressed state, while pulling and stretching the push-rod automatically to restore its original position and prepare for the next measurement.

DESCRIPTION OF THE PREFERRED EMBODIMENTS

The present invention will become clearer in light of the following detailed description of an illustrative embodiment of this invention described in connection with the drawings. It is intended that the embodiments and drawings disclosed herein are to be considered illustrative rather than restrictive.

Figure 1:
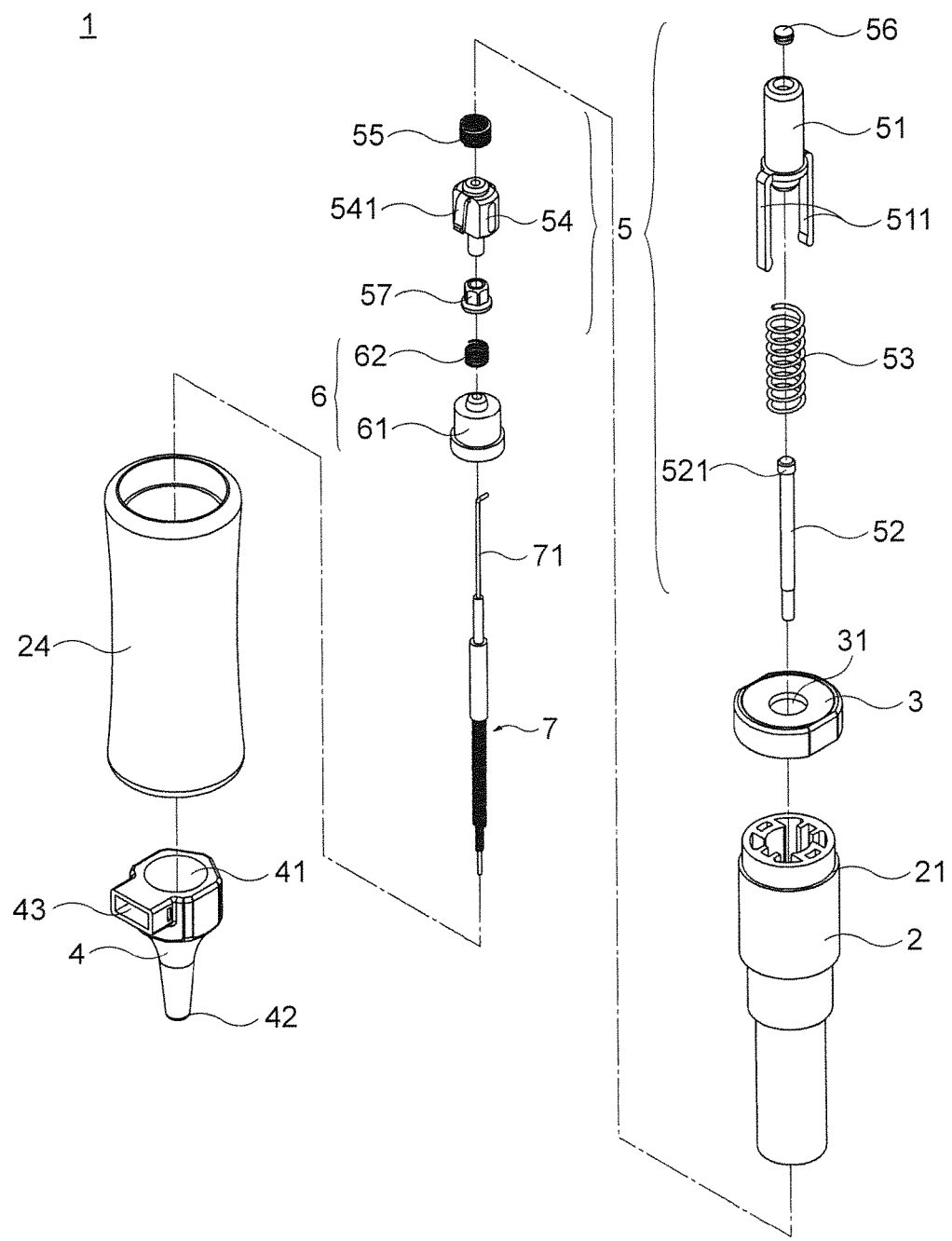
FIG. 1 is an exploded view of the present invention.
Figure 2:
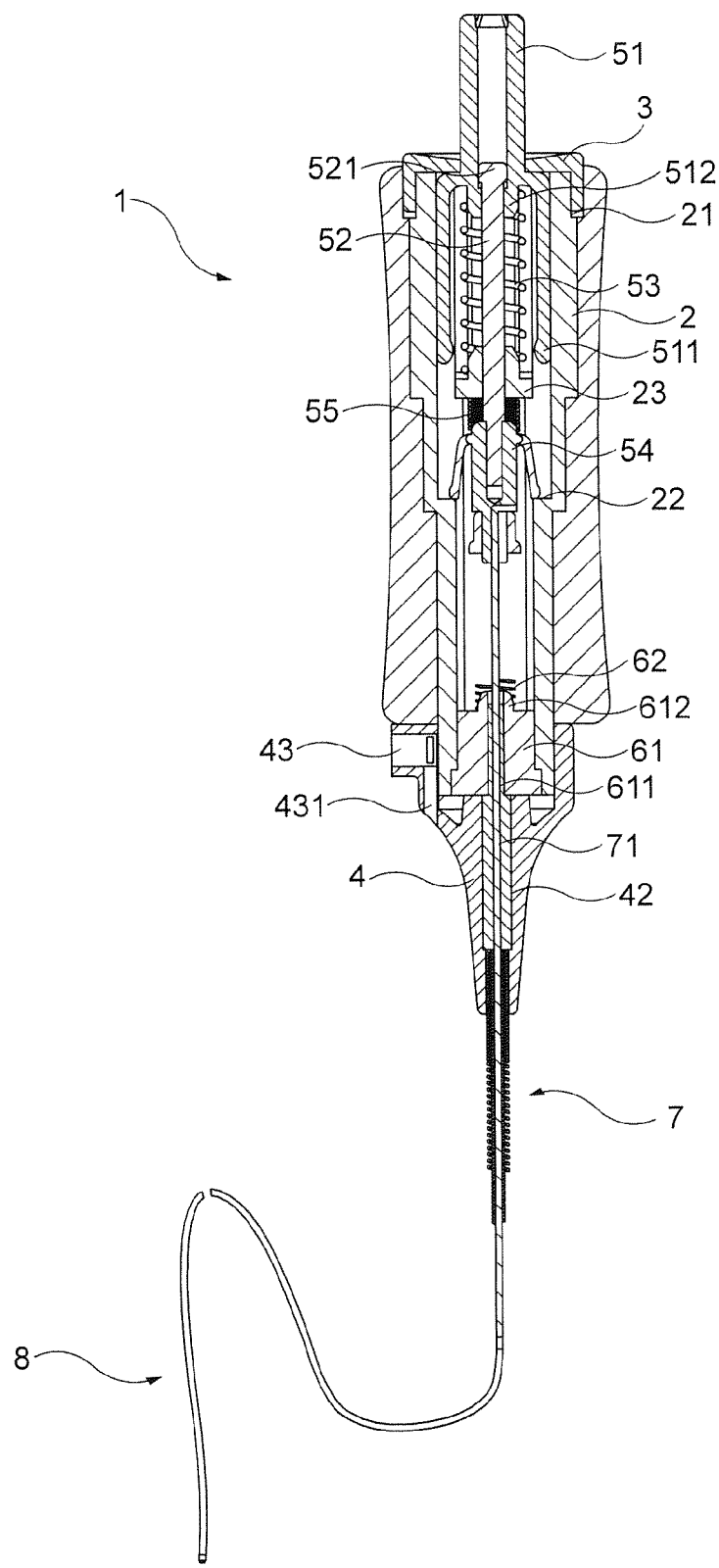
FIG. 2 is a cross-sectional view of the present invention.

With reference to FIGS. 1 and 2 for a firing mechanism applied to an endoscope accessory, the firing mechanism 1 comprises a housing 2, a cap 3, a bottom cover 4, a driving module 5, a buffering module 6, a spring pipeline 7, a push-rod 71 and a detecting module 8. The housing 2 is a hollow tube and comprises an outer embedding wall 21 formed around the external periphery of the housing 2, an inner embedding wall 22 formed inside the housing 2, and a fixed base 23 formed in the hollow tube of the housing 2. The cap 3 is embedded into the outer embedding wall 21 of the housing 2 and has an opening 31. The bottom cover 4 has a groove 41 corresponsive to the housing 2 and combined with the housing 2, a pipeline 42 formed in the bottom cover 4, a connecting portion 43 formed on a side of the bottom cover 4, and a through hole 431 formed on the connecting portion 43. The driving module 5 comprises a pressing device 51, a pull-rod 52, a restoring spring 53, a trigger 54 and a firing spring 55. The pressing device 51 is in form of a hollow tube passing through the opening 31 of the cap 3, and a triggering rod 511 is extended separately from both sides of the pressing device 51, and a convex wall 512 is formed at the center of the pressing device 51, and a bump 521 is formed at the front end of the pull-rod 52 for embedding into the hollow tube of the pressing device 51, and the restoring spring 53 is installed between the convex wall 512 of the pressing device 51 and the fixed base 23 of the housing 2. The trigger 54 has a groove for receiving and fixing an end of the pull-rod 52, and an elastic brace 541 formed separately on both sides of the trigger 54, such that the trigger 54 abuts the inner embedding wall 22 of the housing 2 through the elastic brace 541, and the firing spring 55 is installed between the fixed base 23 of the housing 2 and the trigger 54.

The buffering module 6 comprises a seat body 61 and a buffer spring 62, and the seat body 61 is disposed at an end of the hollow tube of the housing 2 and has a penetrating hole 611. A bump 612 is formed at the top of the seat body 61 and provided for sheathing and fixing the buffer spring 62. The spring pipeline 7 is installed in the pipeline 42 of the bottom cover 4, and the push rod 71 is installed in the spring pipeline 7, such that the front end is fixed to the trigger 54.

Figure 3:
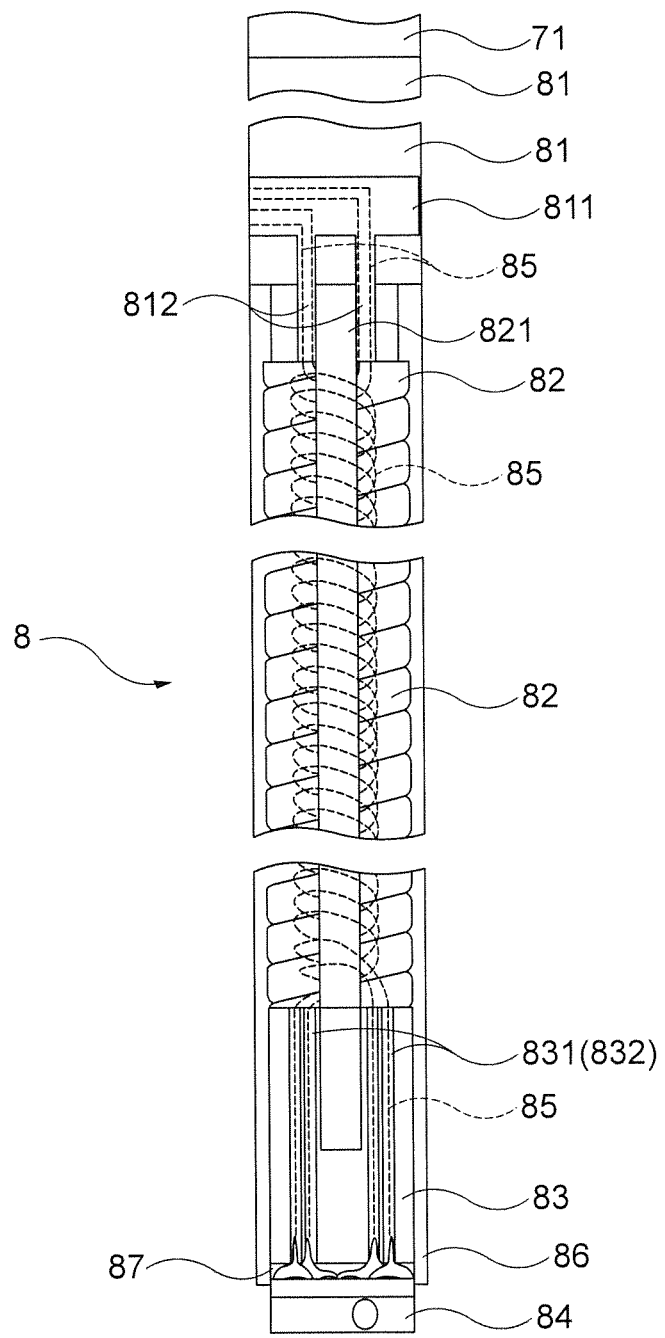
FIG. 3 is a cross-sectional view of a detecting module of the present invention.
Figure 4:
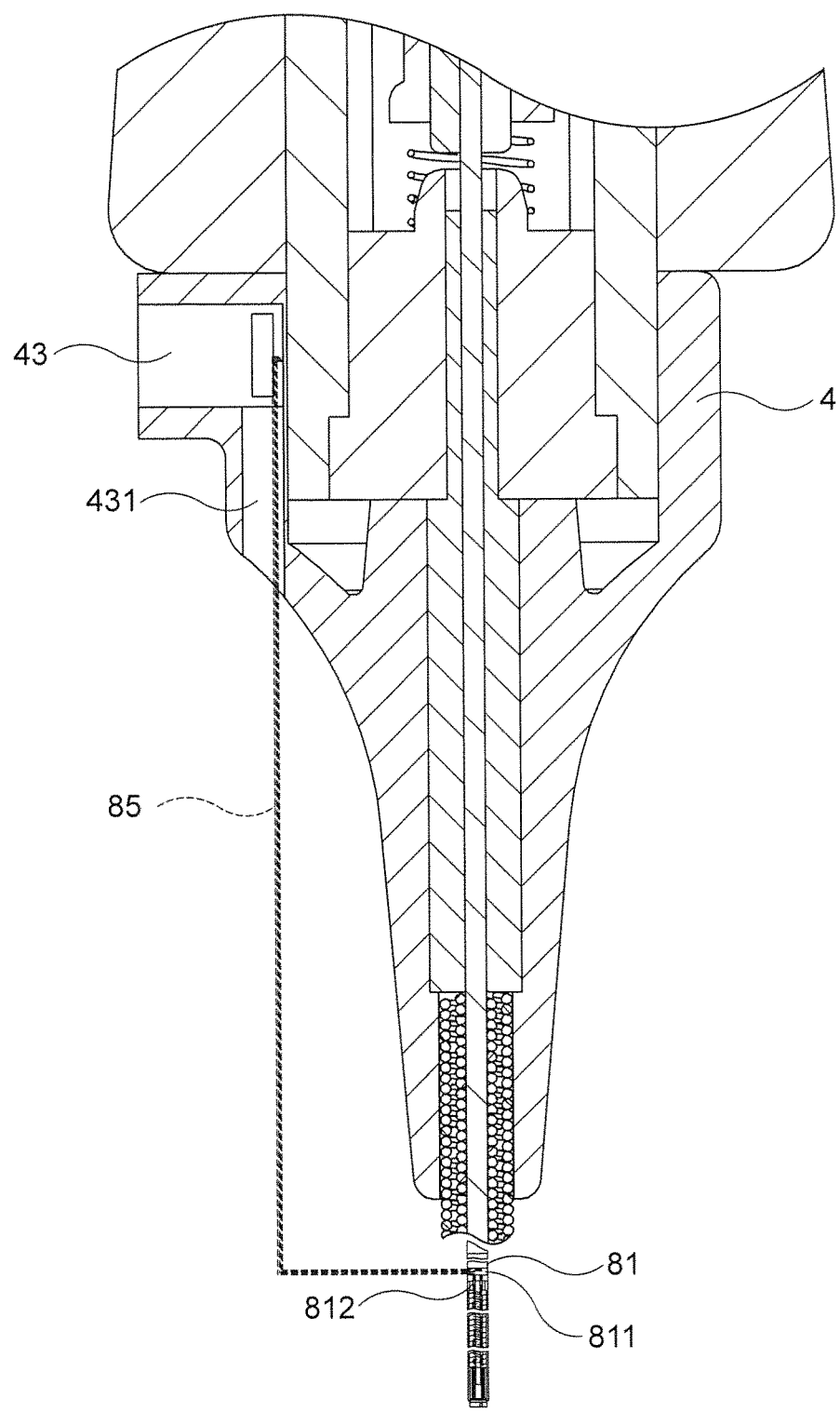
FIG. 4 is a schematic view of connecting a detecting module of the present invention.
Figure 5:
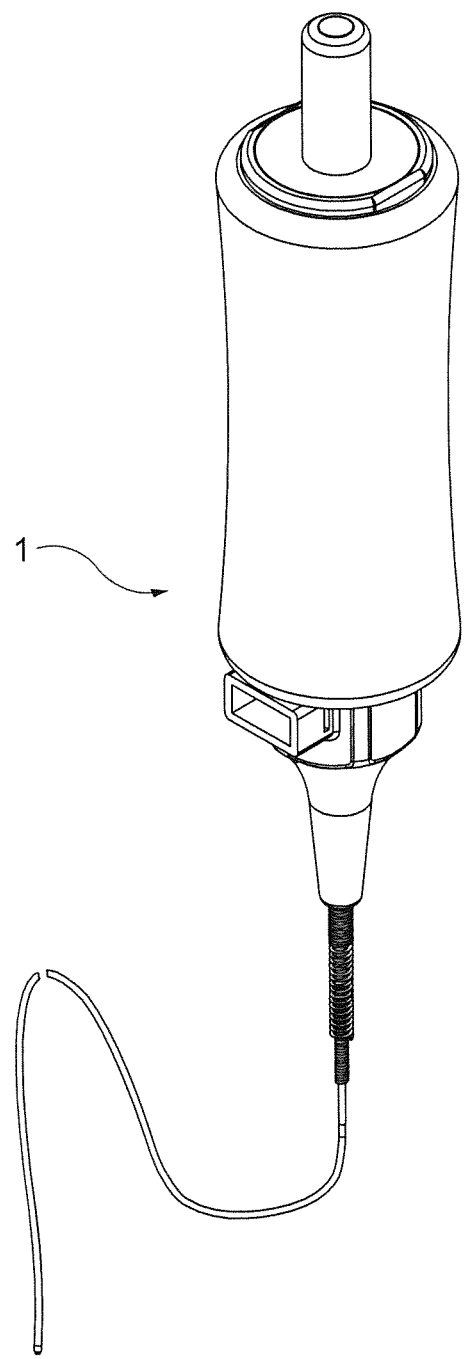
FIG. 5 is a perspective view of the present invention.

As to the detecting module 8 (referring to FIG. 3 for a cross-sectional view of a detecting module of the present invention), the detecting module 8 is combined with an end of the push-rod 71 and the detecting module 8 comprises a front carrier 81 having a perforation 811 and a plurality of holes 812; a spring duct 82 having a core wire 821 fixed therein; a rear carrier 83 having a plurality of holes 831, and a conductive silver paste 832 filled in the holes 831; a sensor 84 coupled to the rear carrier 83; a plurality of conductive wires 85 wound and fixed around the core wire 821 of the spring duct 82, such that after an end of the conductive wire 85 passes through the hole 831 of the rear carrier 83, the end is coupled to the sensor 84, and after the other end passes through the hole 812 of the front carrier 81, such other end is passed through the perforation 811 and connected to the back-end system for reading signals; and a waterproof layer 86 coated on the external periphery of the rear carrier 83 and the spring pipeline 82, Referring to FIGS. 1 to 3 for an assembling process, the housing 2 is placed into a groove 41 of the bottom cover 4, and a seat body 61 is placed onto an end of the housing 2, and a buffer spring 62 is sheathed on the top of the seat body 61, and the trigger 54 is fixed to a push-rod 71. In a preferred embodiment of the present invention, a nut 57 is secured at an end of the trigger 54, so that the push-rod 71 is securely fixed to the trigger 54, and a firing spring 55 is installed between the trigger 54 and the fixed base 23 of the housing 2, and then the pressing device 51 is installed at the front end of the housing 2, and a restoring spring 53 is installed between the convex wall 512 of the pressing device 51 and the fixed base 23 of the housing 2. And then, the pressing device 51 is installed at the front end of the housing 2, and the restoring spring 53 is installed between the convex wall 512 of the pressing device 51 and the fixed base 23 of the housing 2. In a preferred embodiment of the present invention, the hollow tube of the pressing device 51 has a plug 56, and a handle cover 24 is sheathed on the external periphery of the housing 2 to provide users a comfortable grip for the operation. In addition, the pressing device 51 is installed to the cap 3 through the opening 31 and the cap is embedded between the housing 2 and the handle cover 24. The cap 3 is installed to the pressing device 51 through the opening 31 and embedded between the housing 2 and the handle cover 24. In addition, the conductive wires 85 of the detecting module 8 are wound and fixed around the core wire 821 in the spring duct 82, and an end of the conductive wire is passed through the hole 831 of the rear carrier 83. In a preferred embodiment of the present invention, the conductive wires 85 are connected to the sensor 84 by soldering, and an adhesive layer 87 is coated at the soldering position of the rear carrier 83 and the sensor 84, so that the connecting position has a smooth surface, and after the other end of the conductive wire 85 is passed through the hole 812 of the front carrier 81, such end is passed out from the perforation 811 (also see FIG. 4), and then passed into the through hole 431 of the bottom cover 4 and soldered to the connecting portion 43, such that the back-end system can read the signal through the connection with the connecting portion 43. The aforementioned components constitute the firing mechanism 1 (as shown in FIG. 5).

Figure 6:
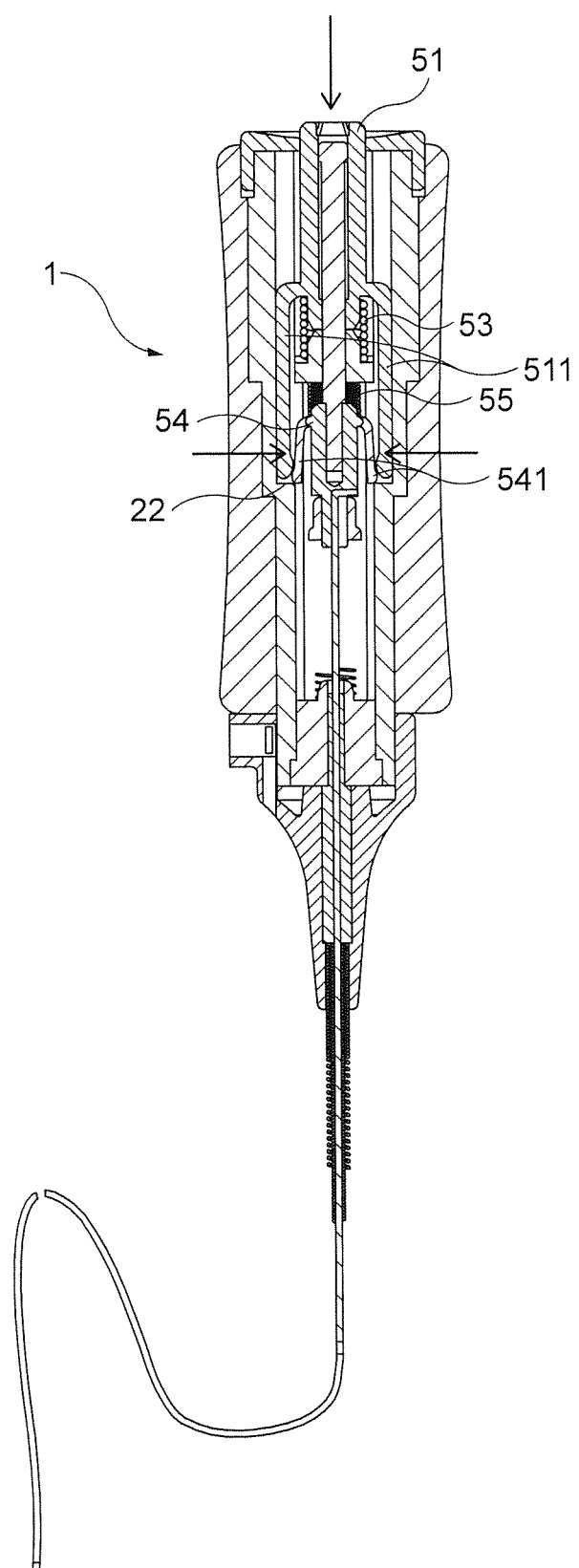
FIG. 6 is a schematic view of pressing down a pressing device of the present invention.

With reference to FIG. 6 for the schematic view of pressing down the pressing device of the present invention pressing device, when the firing mechanism 1 is not in use, the restoring spring 53 is situated at a non-compressed state, and the firing spring 55 is situated at a compressed state. When the pressing device 51 is pressed, the triggering rods 511 on both sides of the pressing device travel for a certain distance and push the elastic braces 541 on both sides of the trigger 54 respectively to compress the restoring spring 53, so that the elastic brace 541 originally abutting at the inner embedding wall 22 is retracted and falls down.

Figure 7:
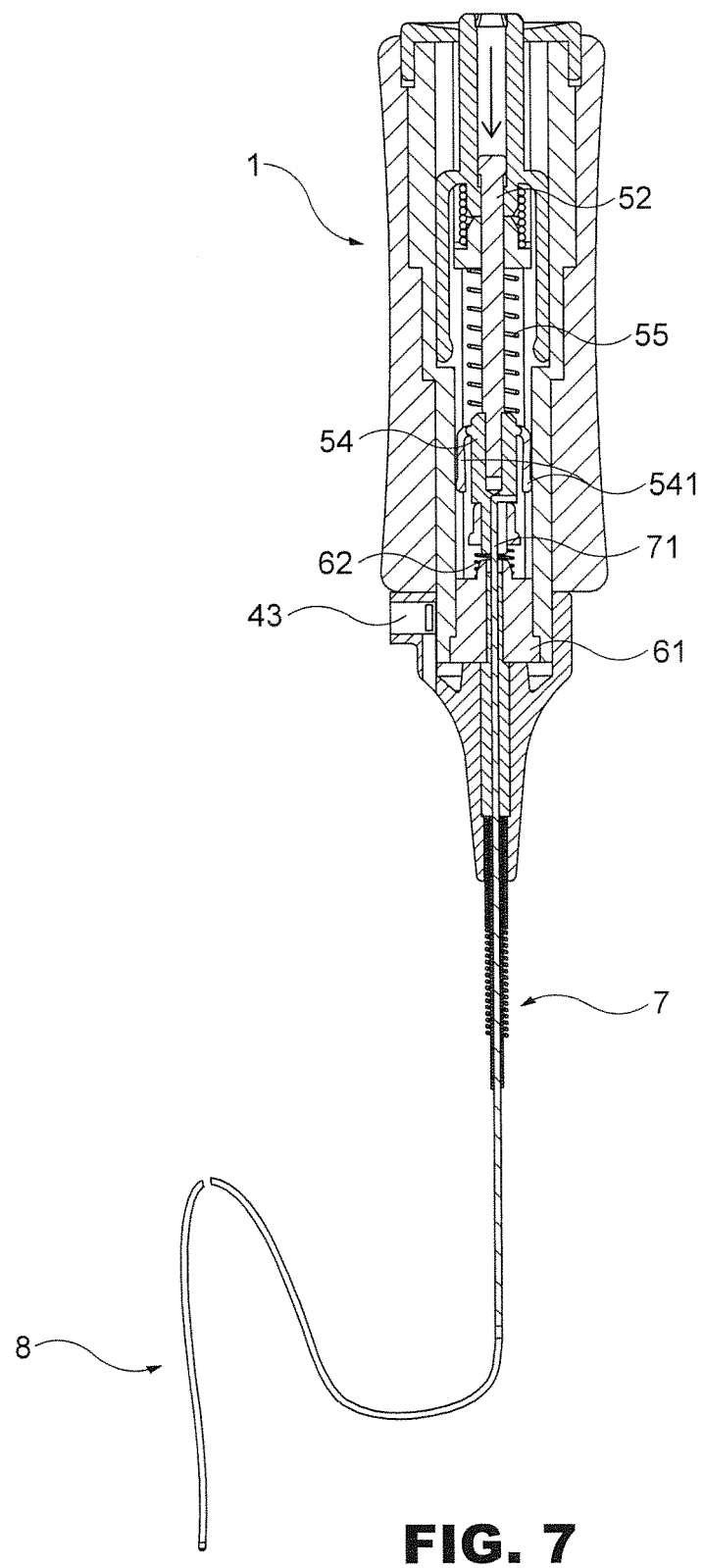
FIG. 7 is a schematic view of pushing out a push-rod of the present invention.
Figure 8:
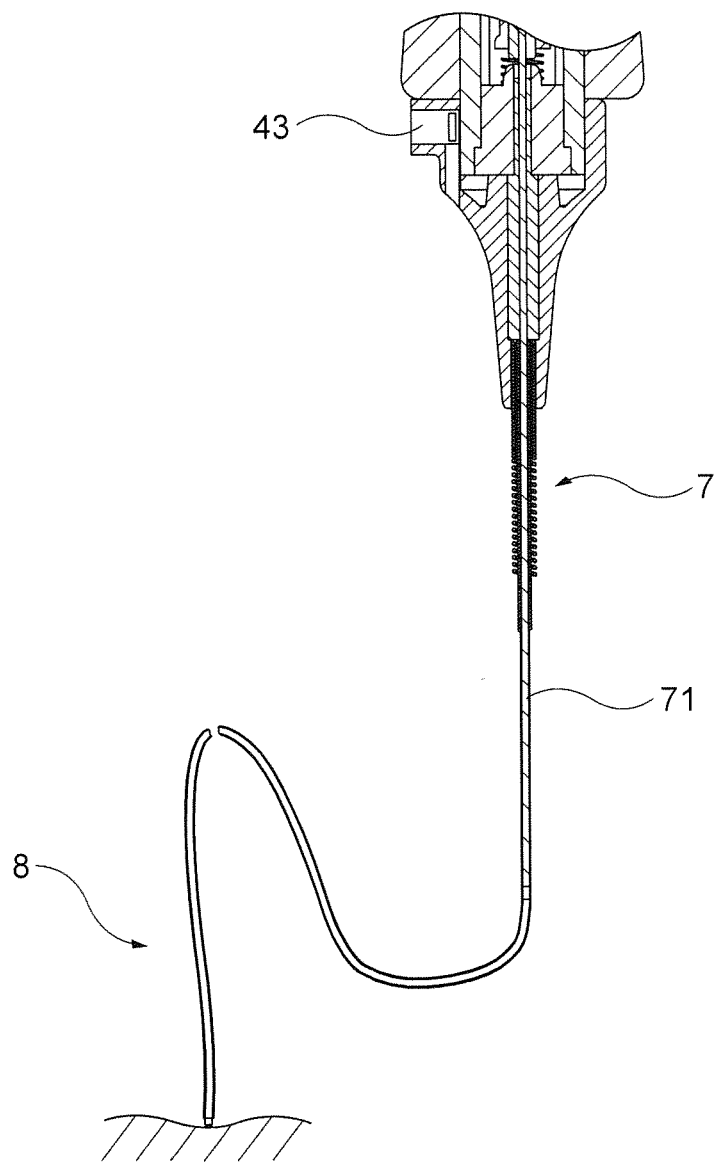
FIG. 8 is schematic view of a measurement of the present invention.
Figure 9:
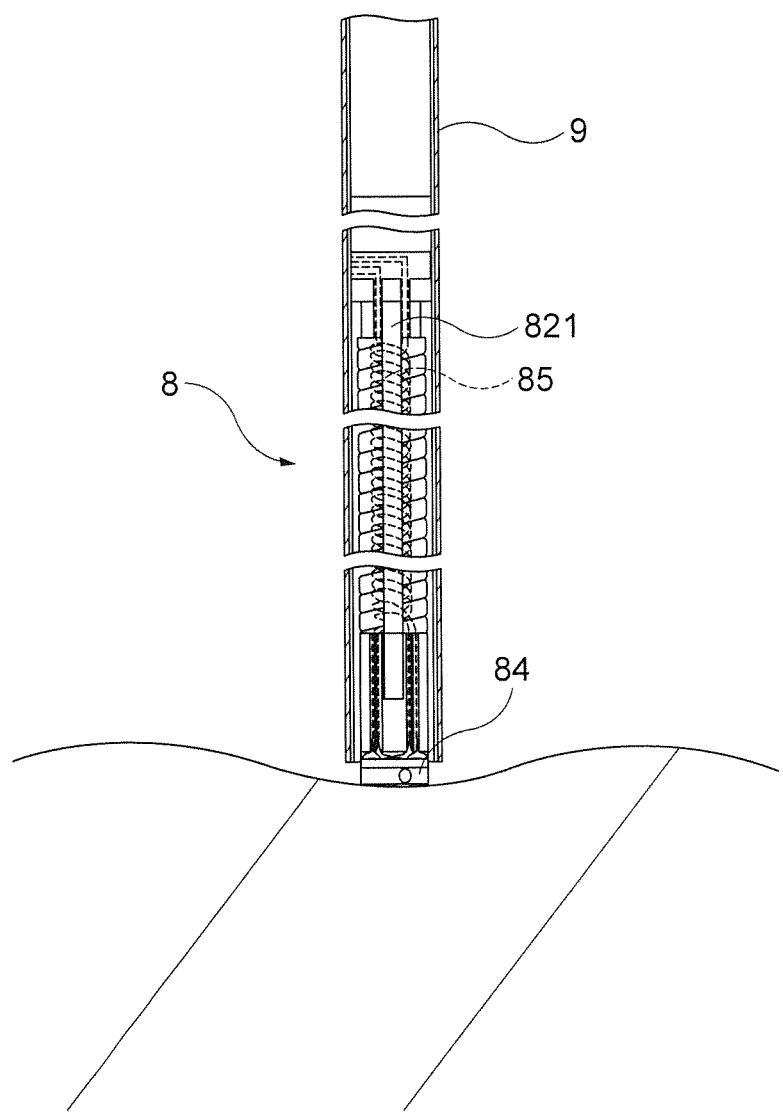
FIG. 9 is schematic view of a measurement taken by a detecting module of the present invention.

In the meantime, the compressed state of the firing spring 55 is released (also see FIG. 7), and the trigger 54 is triggered by the resilience of the firing spring 55 and fired to the seat body 61, and the buffer spring 62 of the seat body 61 provides a buffering effect for the downward pulling force and links the pull-rod 52 and the push-rod 71 in the firing process, so that the push-rod 71 pushes out the spring pipeline 7 (as shown in FIG. 8), such that a detecting module 8 combined with the front end of the push-rod 71 is stretched out through the sensor to touch a tissue to be tested (also see FIG. 9). Since the conductive wires 85 of the detecting module 8 are wound and fixed around the core wire 821, therefore noises produced by the vibration of the sensor 84 may be reduced, and the connecting portion 43 (not shown in the figure) is connected to the back-end system for reading a feedback signal of the sensor 84. If the detected tissues of a living body include any subcutaneous tumor, an abnormal value of the tissue hardness will be detected and provided as a reference to doctors as a basis for diagnosis and determination.

Figure 10:
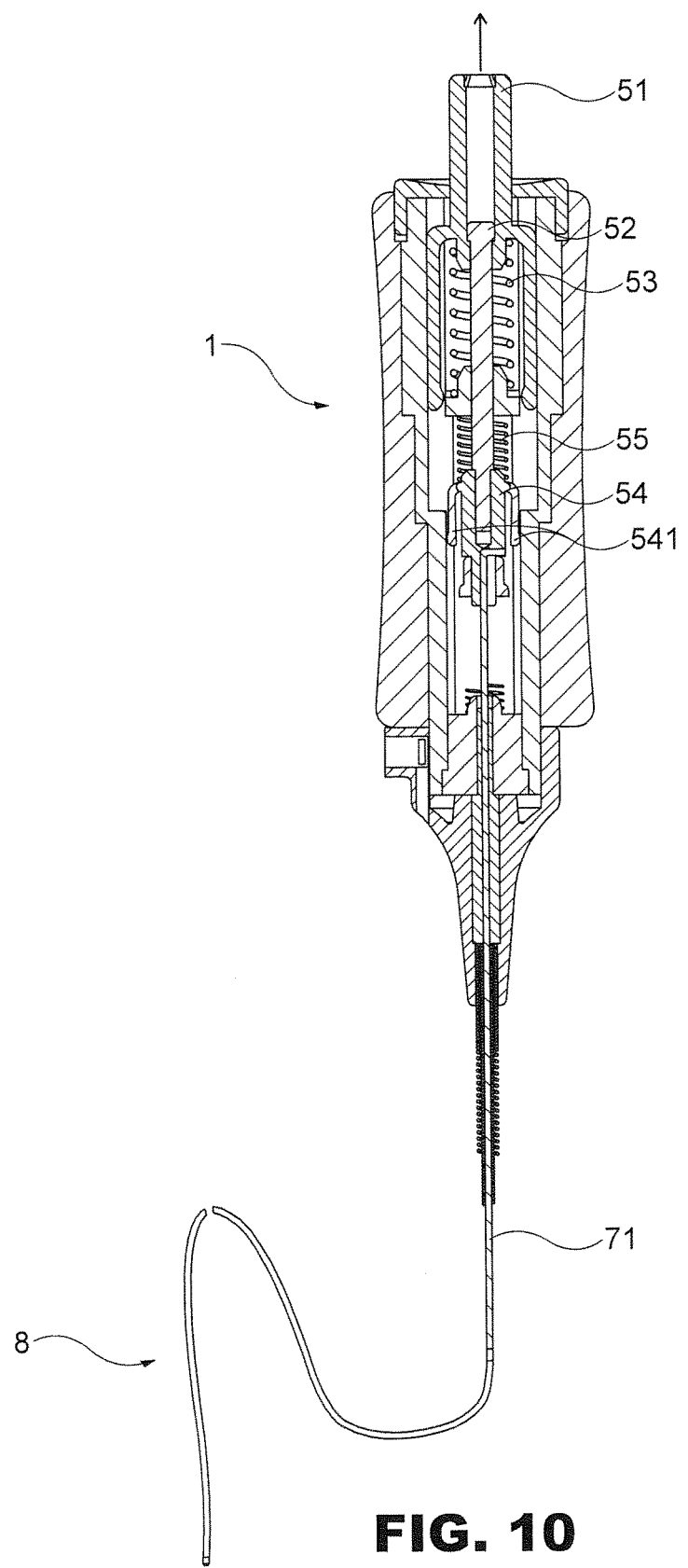
FIG. 10 is a schematic view of pulling back a pressing device of the present invention.
Figure 11:
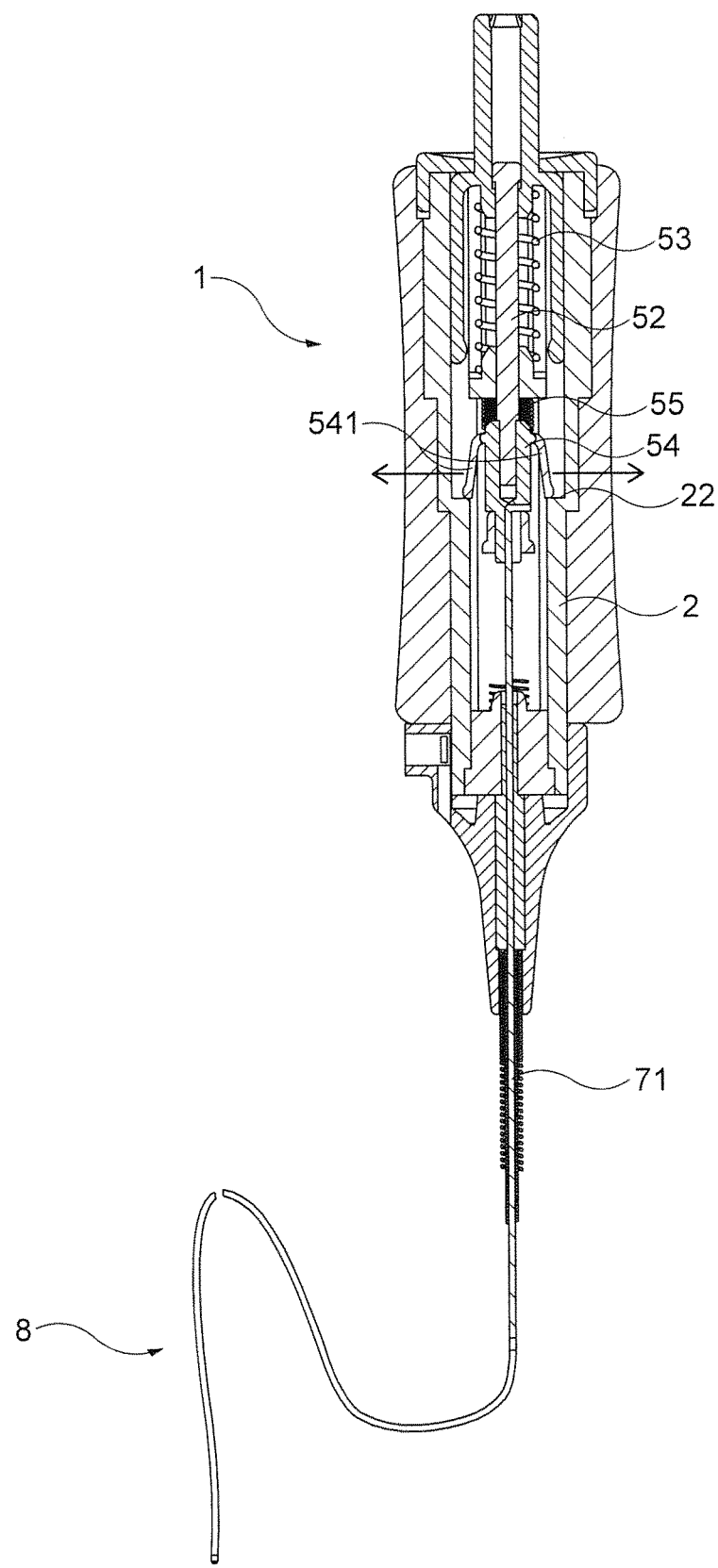
FIG. 11 is a schematic view of the present invention after restoring its position.

If the signal is detected by the detecting module 8 and transmitted back to the back-end system (also refer to FIG. 10 for the schematic view of pulling back the pressing device of the present invention), users may release the pressing of the pressing device 51, so that the compressed state of the restoring spring 53 is released to push the pressing device 51 back to its original position and drive the pull-rod 52 to pull back the trigger 54 accordingly, and the elastic brace 541 of the trigger 54 abuts the inner embedding wall 22 of the housing 2 (also see FIG. 11), and the firing spring 55 resumes its compressed state, while the push-rod 71 is automatically pulled and stretched with the trigger 54 to restore its original position and prepare for the next measurement.

It is noteworthy that the firing mechanism 1 of the present invention forms the reciprocating structure by two springs of different rigidities, wherein the coefficient of rigidity of the firing spring 55 is greater than the coefficient of rigidity of the restoring spring 53, and the required firing force is calculated by Hooke's law, such that after the sensor 9 of the firing mechanism 1 is triggered, the resilience of the restoring spring 53 compresses the firing spring 55 again to its firing length. Therefore, the position restoration can be completed by a single driving point, and the firing operation can be achieved by one hand, so as to simplify the doctor's operation and improve convenience and efficiency.

In summation of the description above, the present invention improves over the prior art, and is thus duly filed for patent application. While the invention has been described by means of specific embodiments, numerous modifications and variations could be made thereto by those skilled in the art without departing from the scope and spirit of the invention set forth in the claims.

What is claimed is:

1. An apparatus for detecting tissue hardness of a living body, comprising:
   a housing, being a first hollow tube, and having an outer embedding wall formed around an outer periphery of the housing, an inner embedding wall formed inside the housing, and a fixed base formed in a tube body of the housing;
   a cap, embedded into the outer embedding wall of the housing, and having an opening;
   a bottom cover, coupled to the housing, the bottom cover including a pipeline formed therein, a connecting portion disposed on a side of the bottom cover, and a through hole formed at the connecting portion; and
   a driving module, comprising:
      a pressing device, being a second hollow tube, and having a triggering rod extended separately from both sides of the pressing device;
      a pull-rod, installed in the second hollow tube of the pressing device;
      a restoring spring, installed between the pressing device and the fixed base;
      a trigger, fixed to the pull-rod, and having an elastic brace formed separately on both sides of the trigger, such that the elastic brace supports and abuts the inner embedding wall of the housing; and
      a firing spring, installed between the fixed base of the housing and the trigger, and having a coefficient of rigidity greater than a coefficient of rigidity of the restoring spring; and
   a buffering module, comprising:
      a seat body, disposed at a first end of the housing, and having a penetrating hole; and
      a buffer spring, sheathed on the seat body; and
   a spring pipeline, installed in the pipeline of the bottom cover;
   a push-rod, installed in the spring pipeline, the push-rod having a front end fixed to the trigger; and
   a detecting module, combined with a back end of the push-rod, and including:
      a front carrier, having a perforation and a plurality of front carrier holes;
      a spring duct, having a core wire fixed therein;
      a rear carrier, having a plurality of rear carrier holes, and a conductive silver paste filled into the rear carrier holes;
      a sensor, combined with the rear carrier;
      a plurality of conductive wires, wound around the core wire, such that after a proximal end of the conductive wires passes through the rear carrier holes of the rear carrier, the proximal ends of the conductive wires are coupled to the sensor, and after a distal end of the conductive wires passes through the front carrier holes of the front carrier, said distal end is passed out of the perforation and connected to a back-end system for reading a signal; and
      a waterproof layer, coated to encapsulate a periphery of the rear carrier and the spring duct.

2. The apparatus for detecting tissue hardness of a living body as claimed in claim 1, further comprising a handle cover sheathed on the outer periphery of the housing.

3. The apparatus for detecting tissue hardness of a living body as claimed in claim 1, further comprising an adhesive layer disposed at a combining position of the sensor and the push-rod.

4. The apparatus for detecting tissue hardness of a living body as claimed in claim 1, wherein the conductive wires and the back-end system are coupled by passing the conductive wires that passes through the perforation into the through hole of the bottom cover and soldering the conductive wires to the connecting portion, so that the back-end system is connected through the connecting portion to read a signal.

* * * * *